United States Patent [19]
Unger

[11] Patent Number: 5,870,190
[45] Date of Patent: Feb. 9, 1999

[54] PARTICLE SENSOR AND RELATED METHOD OFFERING IMPROVED PARTICLE DISCRIMINATION

[75] Inventor: Roger L. Unger, Riverside, Calif.

[73] Assignee: Venturedyne, Ltd., Milwaukee, Wis.

[21] Appl. No.: 977,745

[22] Filed: Nov. 25, 1997

[51] Int. Cl.$^6$ ................................................. G01N 15/02
[52] U.S. Cl. ........................................ 356/336; 356/339
[58] Field of Search ................................. 356/335–343, 356/244, 246, 436, 440; 250/574, 576, 564; 377/11, 10, 53

[56] References Cited

U.S. PATENT DOCUMENTS

| | | | |
|---|---|---|---|
| 3,781,552 | 12/1973 | Kadrmas | 250/206 |
| 4,623,252 | 11/1986 | Hollenbeck | 356/338 |
| 4,984,889 | 1/1991 | Sommer | 356/336 |
| 4,986,657 | 1/1991 | Ohe | 356/73 |
| 4,990,795 | 2/1991 | Suzuki et al. | 356/339 |
| 5,047,963 | 9/1991 | Kosaka | 364/555 |
| 5,194,921 | 3/1993 | Tambo et al. | 356/432 |
| 5,282,151 | 1/1994 | Knollenberg | 364/555 |
| 5,296,910 | 3/1994 | Cole | 356/28.5 |
| 5,325,169 | 6/1994 | Nakamoto et al. | 356/73 |
| 5,424,558 | 6/1995 | Borden et al. | 250/573 |
| 5,432,601 | 7/1995 | Tanaka et al. | 356/246 |
| 5,467,189 | 11/1995 | Kreikebaum et al. | 356/339 |
| 5,515,164 | 5/1996 | Kreikebaum et al. | 356/339 |
| 5,576,827 | 11/1996 | Strickland et al. | 356/336 |

FOREIGN PATENT DOCUMENTS 4-308508  6/1994  Japan .

OTHER PUBLICATIONS

Digital Signal Processing for Optical Particle Counters in Order to Improve the Signal–to–Noise Ratio, Aerosol Science & Technology 25:399–410, Nov., 1966.

*Primary Examiner*—Hoa Q. Pham
*Attorney, Agent, or Firm*—Jansson, Shupe, Bridge & Munger, Ltd.

[57] ABSTRACT

A method for counting, by ranges of size, particles flowing through a particle sensor including the steps of flowing a particle through the sensor, thereby producing a voltage pulse which is sampled over a period of time. Sampling yields a plurality of voltage values which includes a latest value and a former value. The latest value is compared with the former value and when less than the former value, the method finds, in a table of threshold voltages, the size range for the particle. A counting bin corresponding to the size range for the particle is then incremented. The former value may be the value immediately preceding the latest value or it may be several "counts" prior to such latest value. The new particle sensor has an inlet, sensing volume, exhaust port, light collection system and an electronic system coupled to the light collection system. The electronic system is programmed to count particles, by size, in any of several unique ways. Depending upon the embodiment, the method and sensor offer improved discrimination to help avoid counting floaters, false peaks and the like.

20 Claims, 7 Drawing Sheets

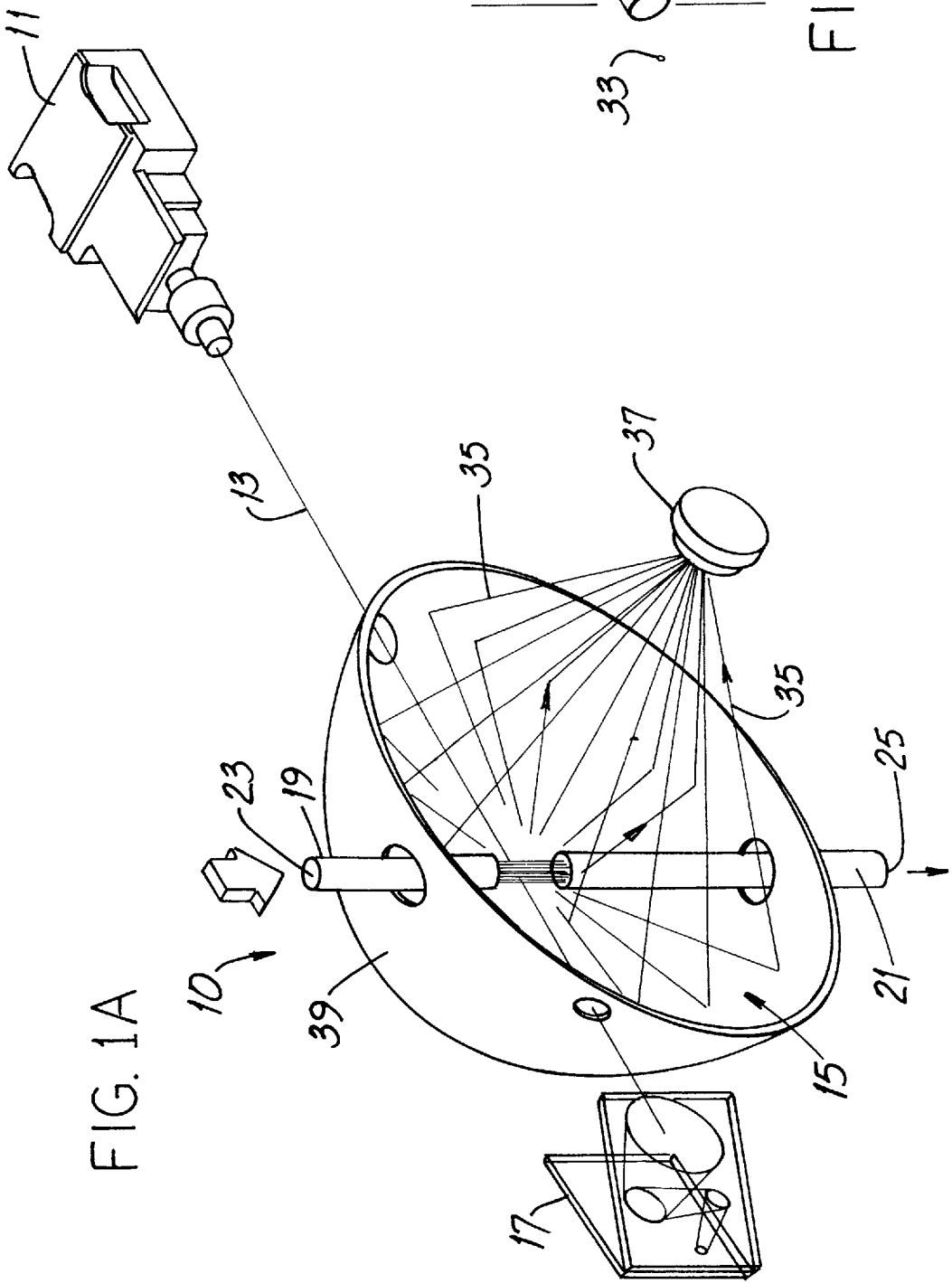

PARTICLE SENSOR AND RELATED METHOD OFFERING IMPROVED PARTICLE DISCRIMINATION

FIELD OF THE INVENTION

This invention relates generally to optical measuring and testing and, more particularly, to counting particles by size and by using light scattering.

BACKGROUND OF THE INVENTION

Counters and sensors are used to detect light scattered by particles entrained in a stream of fluid, e.g., in an air stream. In general, such counters and sensors have a very-small-diameter, highly intense laser beam. The air stream and any particle entrained therein is drawn through the light beam. In the vernacular of the industry, the small spatial region formed by the intersection of the air stream and the laser beam is called the "sensor volume" or the "view volume."

When light strikes the particle, it is scattered. Reflectors direct the scattered light to a photodetector which emits an electrical current pulse, the amplitude of which is generally proportional to the intensity of the light impinging upon it. And, of course, light intensity is a measure of particle size.

Some types of sensors flow air along an enclosed transparent tube; others "project" the air and accompanying particles at a particular flow rate (often measured in cubic feet per minute) from one tube across an open space to another tube. In sensors of the latter type, there is no tube wall (however transparent such wall may be) to impair light scattering and collecting. In other words, the particle is briefly illuminated by a light beam as it "flies" through an open space.

Among other uses, particle counters incorporating particle sensors are used to obtain a measure of air quality by providing information as to the number and size of particles present in some specified volume of air, e.g., a cubic meter of air. Even work environments which appear to human observation to be clean—business offices, manufacturing facilities and the like—are likely to have substantial numbers of airborne particles. While such particles are not usually troublesome to the human occupants, they can create substantial problems in certain types of manufacturing operations.

For example, semiconductors and integrated chips are made in what are known as "clean rooms," the air in which is very well filtered. In fact, clean rooms are usually very slightly pressurized using extremely clean air so that particle-bearing air from the surrounding environs does not seep in. And the trend in the semiconductor and integrated chip manufacturing industry is toward progressively smaller products.

A small foreign particle which migrates into such a product during manufacture can cause premature failure or outright product rejection even before it is shipped to a customer. This continuing "miniaturization" requires corresponding improvements in clean-room environments (and in the related measuring instruments) to help assure that the number and size of airborne particles are reduced below previously-acceptable levels.

Factories making semiconductors and integrated chips are not the only sites at which particle sensors may be used. Makers of pharmaceutical products have applications for such sensors to help exclude foreign matter from medicines and drugs.

Particles which are of concern in clean room and pharmaceutical working environments range in size from a few microns down to so-called "submicron," i.e., 0.1 micron or even smaller. (To give an idea of relative size, it is said that a particle 10 microns in size is about as small as can be seen with the unaided human eye.)

And when operating a particle sensor in such environments, it is preferred to measure the number of particles of each of several different size ranges which pass through the sensor per unit time. The computerized part of the sensor is configured with "bins," i.e., counting registers which add a count based upon data for each of several sizes of particles. For example, the computerized bins may be configured to respectively count particles 0.1 to 0.2 microns in size, particles from 0.2 to 0.3 microns, particles from 0.3 to 0.4 microns and so forth.

Known particle sensors use both analog and digital techniques to determine certain aspects of particles passing through them. For example, U.S. Pat. No. 5,047,963 (Kosaka) discloses an apparatus configured for blood cell analysis. Data regarding the cell nucleus (rather than the entire cell which, compared to particles of concern in clean room analysis, is quite large) is processed using a digital signal processor.

U.S. Pat. No. 4,984,889 (Sommer) discloses a particle size measuring system which uses analog pulses from a photodetector. Such pulses result when a particle passes through the system. It is understood that only the peak amplitude of an analog input pulse is digitized and registered in a computer or the like to increment "counts" of particles of differing sizes. U.S. Pat. No. 4,623,252 (Hollenbeck) discloses a particulate counter which digitizes an analog output. A comparator compares the signal to a threshold voltage value and if the threshold is exceeded (which is interpreted to represent detection of a particle), a sampler performs over 200 samples of the A/D converter output. The single maximum sample is selected and the lesser samples are disregarded.

U.S. Pat. No. 5,424,558 (Borden et al.) also mentions using digital signal processing to perform particle analysis but there is scant information as to how this is done. The Borden et al. apparatus is capable of a type of dynamic tuning, i.e., adjustments to bandwidth and gain to accommodate different types of signal pulses.

While these and other known particle sensors have been generally satisfactory for their intended purposes, they are not without disadvantages. For example, it is highly preferred to be able to distinguish a particle which is to be sized and counted from some sort of "floater," i.e., a vagrant speck of material which passes through the light beam. Such a speck may have simply stuffed off of a tube or housing wall. Some counters, like that of the Hollenbeck patent, count signal peaks or crossings of a photodiode output voltage which exceeds some threshold voltage. In a counter of this type, a floater may produce several false counts.

Another disadvantage of known approaches is evident in the Borden et al. apparatus. Such apparatus cannot be dynamically reconfigured (reconfigured while in operation) to change the value and number of thresholds which define the particle size bins. For greatest flexibility in operation, this would be a desirable feature.

A new particle sensor which addresses disadvantages of known sensors would be an important advance in this field of technology.

OBJECTS OF THE INVENTION

It is an object of the invention to provide a new particle sensor and related method which address some of the problems and shortcomings of the prior art.

Another object of the invention is to provide a new particle sensor and related method which more accurately count and size particles.

Another object of the invention is to provide a new particle sensor and related method which better distinguish between significant particles and vagrant, insignificant floaters, i.e., tiny bits of matters for which no counting and sizing is to be performed.

Yet another object of the invention is to provide a new particle sensor which can be dynamically configured to change the value and number of the pulse voltage thresholds which define the particle size bins.

Another object of the invention is to provide a new particle sensor which helps avoid counting false peaks caused by background noise. How these and other objects are accomplished will become apparent from the following descriptions and from the drawings.

SUMMARY OF THE INVENTION

A particle sensor uses scattered light for counting, by ranges of size, particles entrained in fluid drawn from an environment into the particle sensor. In an exemplary embodiment, the sensor includes an inlet through which a particle is drawn from the environment being monitored, e.g., a "clean room" in a manufacturing plant. The sensor has a sensing volume defined by the intersection of a light beam and a fluid stream flowing from the inlet. The sensor also has an exhaust port through which the fluid exits the sensor after passing through the sensing volume.

An optical light collection system redirects light scattered by the particle in the sensing volume to a photo detector circuit which emits an electrical pulse representing the size of the particle. In a specific embodiment, the pulse is a shaped voltage pulse based upon a current pulse from the photo detector. An analog-to-digital converter is coupled to the circuit and samples the pulse at least twice. Pulse "sampling" is by taking "readings" of the different voltage values along the pulse.

A digital signal processor is coupled to the converter and a microcontroller coupled to the processor. The processor and the microcontroller are programmed to carry out a method for counting, by ranges of size, the particles flowing through the particle sensor. As will become apparent, the method programmed into the sensor may include any one or more of several variations as described below.

Carrying out the method results in counting, by ranges of size, particles flowing through the particle sensor. The method includes establishing particle size ranges in a computerized table of threshold voltages. A specific table will include progressively increasing particle sizes and progressively increasing voltages, each corresponding to a particle size.

A particle eventually flows through the sensor and creates a pulse, e.g., a current pulse, resulting from light scattered by the particle. In a specific method, the current pulse is inverted and re-shaped to a voltage pulse which retains the amplitude/charge relationship of the original pulse.

Over a period of time, a plurality of voltage values are sampled along the voltage pulse and such plurality includes a latest value and a former value. The latest value is repetitively compared with the former value and when it is less than the former value, the sensor finds, in the table, the size range for the particle. Having identified the size range, a counting "bin" corresponding to that size range is incremented.

Certain variants of the method may use noise-level voltage and/or baseline voltage as a parameter or as parameters. (A noise-level voltage is a voltage "read" by the A/D converter which results from unwanted but largely unavoidable disturbances, i.e., "noise," in the sensing cavity. A baseline voltage is the nominal voltage value read by the A/D converter when no particles are present in the sensor.

In more specific aspects, the establishing step also includes identifying a noise-level voltage and the finding step occurs only when the latest value exceeds the noise-level voltage. The establishing step may also include identifying the baseline voltage and repeating the finding and incrementing steps only after the latest value is below the baseline voltage. This technique helps reduce false counts caused by vagrant particles.

It has been observed that a voltage pulse caused by a particle will be substantially shorter in duration that a voltage pulse resulting from a vagrant particle floating around in the sensing cavity. In another aspect of the invention, the sampling step includes starting a timer when any of the plurality of voltage values caused by a particle, legitimate (to be counted) or vagrant, exceeds the noise-level voltage. The finding step occurs only if the duration of the pulse is not greater than some predetermined maximum time. This technique significantly reduces false counts caused by vagrant particles.

In another aspect of the method, the pulse caused by a particle to be sampled has a peak value. The plurality of voltage values sampled includes 1 through "n" samples defining an arithmetic progression. The latest value is the sample "n" and the former value is the sample (n−1) and is the peak value. A sensor and its converter having a slow sampling rate may be characterized by this aspect of the method.

But if the converter has a relatively high sampling rate, the latest value is the sample "n" and the former value is the peak value and is the sample (n−a) where "a" is an integer. The integer may be relatively large, i.e., 20, 50 or even higher. (One would expect to see higher sampling rates as the speed of converters and their related "chips" increases and their costs diminish.

Further details of the invention are set out in the following detailed description and in the drawings.

BRIEF DESCRIPTIONS OF THE DRAWINGS

FIGS. 1A and 1B, taken together, depict hardware and electronic system aspects of the new sensor.

FIG. 2 is a perspective view, greatly enlarged of a sensing volume shown in FIG. 1A.

DETAILED DESCRIPTIONS OF PREFERRED EMBODIMENTS

The invention involves a new particle sensor 10 and a related new method. The first part of this specification describes how the new sensor 10 is arranged.

The Arrangement of the Particle Sensor

Figure 1B:
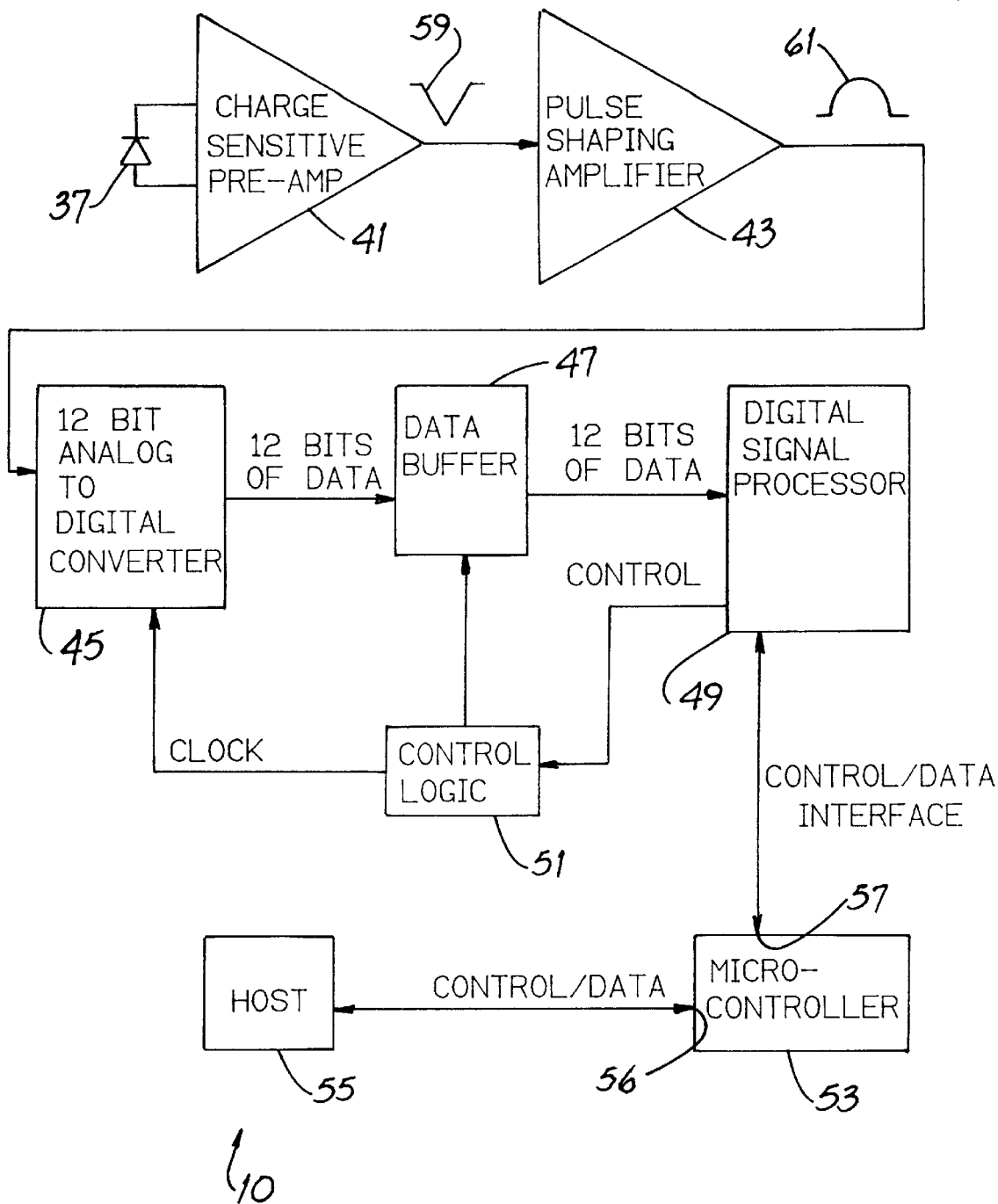

Referring to FIGS. 1A, 1B and 2, the particle sensor 10 includes a source of light 11 such as a laser diode source which together with one or more focusing lens (not shown) provides a very-small-diameter beam of light 13 projected through a sensing cavity 15 to a light-killing trap 17. A pair of fluid flow tubes 19, 21, provide an inlet 23 and an exhaust port 25, respectively, for fluid drawn from a room or other environment in which the size and number of particles is being monitored.

The flow path 27 and the beam of light 13 intersect and define a sensing volume 29, often referred to as a view volume. When a particle 31 from an environment from which samples are being drawn, e.g., a room, is to be counted by size, or when a vagrant particle 33, e.g., a tiny bit of material emanating from the sensor itself and floating around in the cavity 15, passes through the beam 13, either type of particle 31, 33 reflects light. Light reflected by a particle 31 or 33, represented by the arrows 35, either impacts a photodiode 37 directly or after having been reflected by an optical light collecting system such as an elliptical mirror 39. The photodiode 37 emits a current pulse which, after conversion to a "smoothed" voltage pulse, is analyzed by the electronic system shown in FIG. 1B to ascertain the size of the particle 31 and to count it in the appropriate size category. As will become apparent, certain aspects of the invention help avoid counting the vagrant floater particle 33 as a bona fide particle 31 drawn from the environment being monitored.

The electronic system includes a pre-amplifier 41 (preferably of the charge-sensitive type), a pulse-shaping amplifier 43, an analog-to-digital (A/D) converter 45 (e.g., a 12 bit device, type XRD8794), a data buffer 47, a digital signal processor 49 or "DSP" (of the type TMS320C50, for example), a control logic section 51, a microcontroller 53 (e.g., type PIC16C74) and a host computer 55.

The microcontroller 53 is used to interface the processor 49 to the host computer 55. This frees the processor 49 to process the data stream when the microcontroller 53 is communicating with the relatively slower computer 55. The microcontroller 53 has a flexible interface port 56 (parallel or serial) through which it receives commands (e.g. start sampling, stop sampling, set thresholds, etc.) and returns the particle counts. The microcontroller's interface port 57 to the processor 49 mainly involves issuing control commands and receiving the accumulated counts.

The computer 55 accepts operator commands and receives the counts for display. Such computer 55 may be embodied as an external computer, e.g., a desktop personal computer, or as a computer built as part of the sensor 10 so that such sensor 10 is of the "standalone" type needing no connection to any outside computer.

Operation of Particle Sensor

This part of the specification describes the operation of one embodiment of the sensor 10. Included is a description of how particle counting, by particle size, is carried out.

When a particle 31 or 33 passes through the sensing volume 29, it scatters light and as described above, such light impinges upon the light-sensitive photodiode 37 which puts out an electrical signal in response to such light. The photodiode 37 emits a small current pulse, the magnitude of which is generally proportional to the magnitude of the light energy (in photons) which strikes the photodiode 37. And, of course, the magnitude of the light energy is an indication of particle size. This current pulse is then amplified by the pre-amplifier 41 which generates a voltage pulse 59 proportional to the total charge created by the photodiode 37. (The pulse 59 is shown "negative going" in FIG. 1B).

The amplifier 43 also performs pulse shaping by inverting and smoothing the voltage pulse 59 to an analog, positive-going voltage pulse 61 which retains the amplitude/charge relationship of the pulse 59. (It is to be appreciated that the pulse 59 from the pre-amplifier can be directed to two or more pulse-shaping amplifiers 43 connected in parallel. For purposes of explanation, only a single amplifier 43 is shown.)

Figure 3:
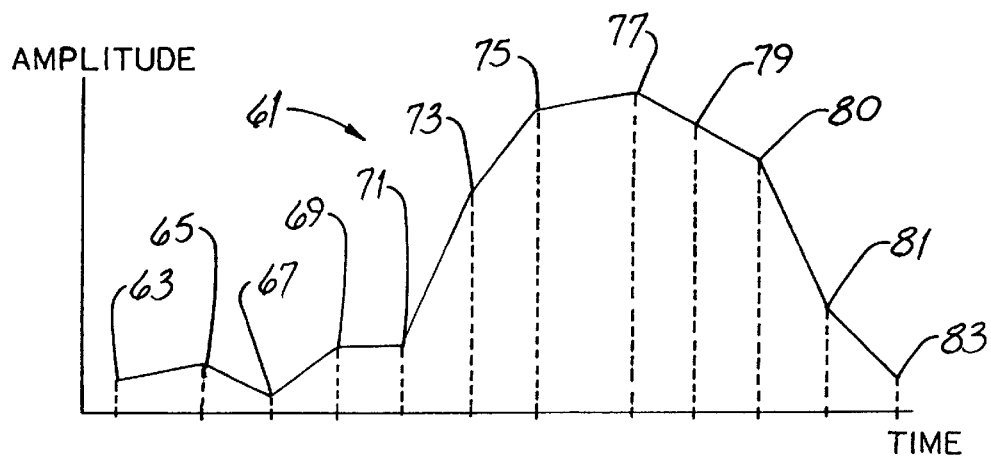
FIG. 3 is a graph showing how points along a voltage pulse are sampled.

Referring also to FIG. 3, the pulse 61 is directed to the A/D converter 45 which, over a very brief period of time, "samples" points on the pulse 61, e.g., points 63, 65, 67, 69 by sequentially converting the analog voltage values at such points to digital-equivalent values. Conversion (or sampling) is carried out continuously and at a fixed rate; that is, the converter 45 converts a point on the pulse 61 to a digital-equivalent value once for each unit of time of fixed duration.

When a 12 bit converter is used, the result of each sampling and conversion is a stream of 12 bit digital numbers which are fed through the buffer 47 and read one at a time by the processor 49. The control logic section 51 assures generation of proper clock timing and control signals.

Expressed in analog terms, each point on the pulse 61 is in voltage units of measure as shown in Table 1 below. (In fact, the converter 45 converts the analog value of each point to a digital-equivalent value and the processor 49 "reads" those digital-equivalent values. In a digital-equivalent value, each point on the pulse 61 is represented by a binary number made up of a 12 digit string of 0s and 1s. An arbitrary example of a 12 bit binary number is 001011001010.

(The specification is written as if the converter 45 and processor 49 are using analog values when, in fact, digitized values are used. For example, "noise" and "baseline" voltage values are described in analog terms but the processor 49 "reads" them as digitized values. Virtually all modern computing systems are described in analog terms but configured to use binary or digitized numbers.)

TABLE 1

VOLTAGE VALUES OF POINTS SAMPLED ALONG PULSE OF FIG. 3

| SAMPLE NO. | VALUE, mV |
| --- | --- |
| 1 | 10 |
| 2 | 16 |
| 3 | 6 |
| 4 | 25 |
| 5 | 25 |
| 6 | 64 |
| 7 | 90 |
| 8 | 97 |
| 9 | 81 |
| 10 | 73 |
| 11 | 34 |
| 12 | 9 |

In FIG. 3 and Table 1, point 63 corresponds to the 1st sample, points 65, 67, 69, 71, 73, 75, 77, 79, 80, 81 and 83 correspond to the 2nd through 12th samples, respectively. The first sampling "reads" the point 63 to have a value of 10, the second sampling reads the point 65 to have a value of 16 and so forth. The processor 49 uses the numbers in the righthand column of Table 1 to determine the peak value of the amplifier output. In the example of FIG. 3 and Table 1, the peak value would be 97 which, as further described below, relates to the size of the particle 31 which scattered the light. The precise ways in which the righthand column numbers are or may be used are described below.

Figure 4:
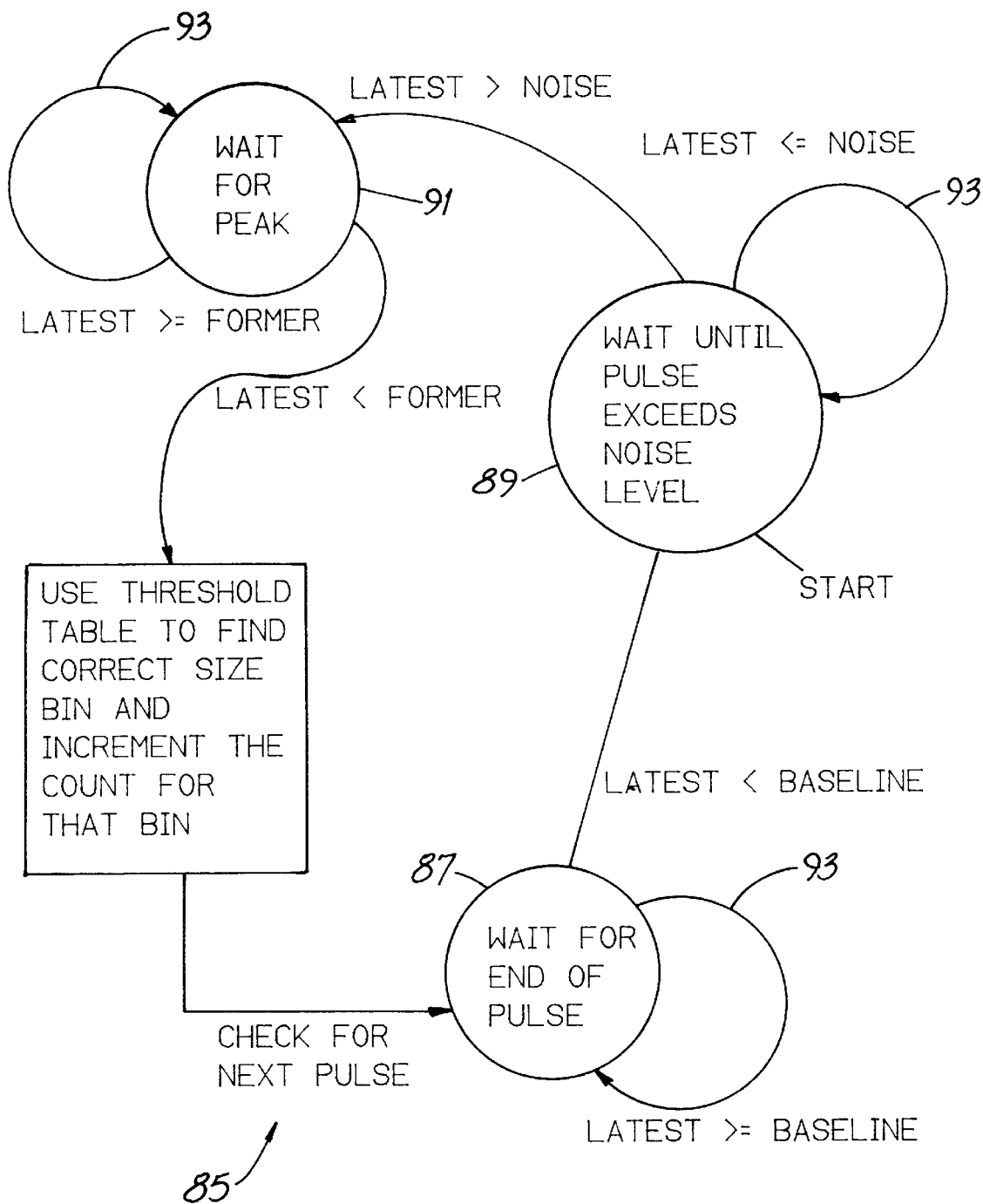
FIG. 4 shows, in diagram form, one of the algorithms with which the new sensor may be programmed.

Referring also to FIG. 4, in one embodiment, the processor 49 is programmed with the diagrammed algorithm 85. Briefly explained, the processor 49 programmed with the algorithm 85 of FIG. 4 extracts the peak value (like value 97 at point 77) from each of successive pulses (like the pulse 61) and keeps a count of the number of particles 31 that fall between various "thresholds."

A table of threshold values may be established in the electronic system in a known manner. An exemplary table of threshold values is set out below.

TABLE 2

| | |
|---|---|
| 0.3000µ | 18.9 mV |
| 0.4000µ | 36.2 mV |
| 0.5000µ | 60.1 mV |
| 0.6000µ | 90.9 mV |
| 0.7000µ | 129 mV |
| 0.8000µ | 149 mV |
| 0.9000µ | 167 mV |
| 1.000µ | 195 mV |
| 1.100µ | 210 mV |
| 1.200µ | 230 mV |
| 1.300µ | 252 mV |
| 1.400µ | 264 mV |
| 1.500µ | 270 mV |
| 1.600µ | 277 mV |
| 1.700µ | 285 mV |
| 1.800µ | 293 mV |
| 1.900µ | 301 mV |
| 2.000µ | 309 mV |
| 2.100µ | 320 mV |
| 2.200µ | 330 mV |

Noting Table 1, the exemplary peak value of the pulse shown in FIG. 3 is 97, the units of measure of which are mV. Noting Table 2, 97 is greater than the threshold 90.9 mV but less than the threshold 129 mV, those threshold values having been selected to correspond to particle sizes. Therefore, the processor 49 will count the particle 31 which created the pulse as one having a size of between 0.6000µ and 0.7000µ.

Counting by size occurs after the algorithm 85 begins sampling a pulse 61. Each "bubble" 87, 89, 91 in the diagram corresponds to a unique state of the algorithm 85 the arrows 93 indicate that the algorithm 85 will recycle through that state until a condition is detected which causes entry into the next state.

Operation of Sensor with Algorithm of FIG. 4

In this specification and unless otherwise defined, the term "latest," "latest value" or similar expressions refer to the voltage value along the pulse 61, for example, which is the most recently occurring in time. The term "former," "former value" or similar expressions refer to that voltage value immediately prior to the latest value.

Figure 5:
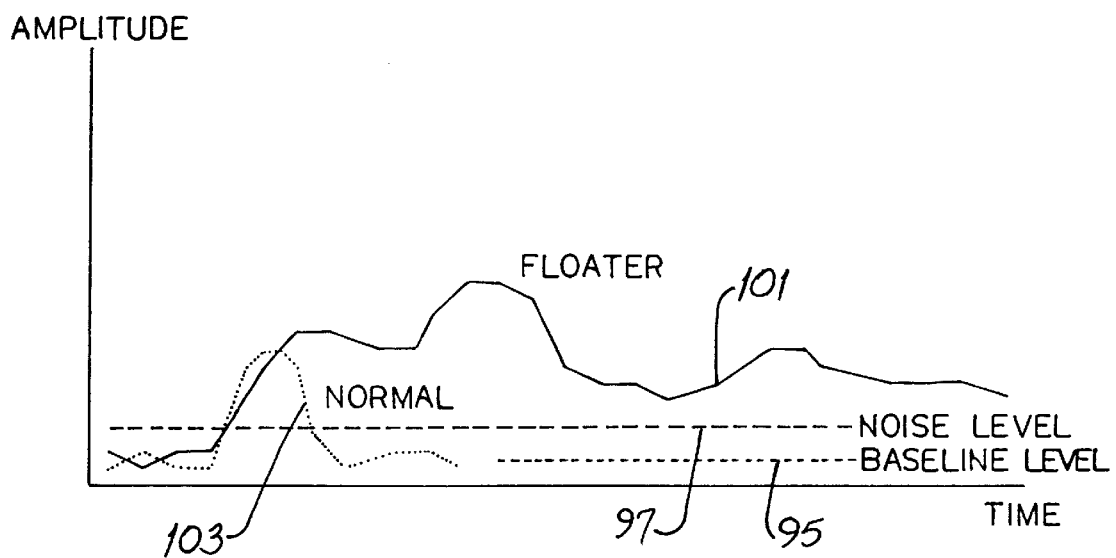
FIG. 5 is a graph showing voltage pulses represented by a floater and by a particle to be counted and also showing noise level and baseline voltages.

Considering FIG. 5, it will also be helpful to understand that the term "baseline" is the voltage value 95 to which the amplifier 43 is expected to return to when no particles are present in the sensor 10. The term "noise" is the maximum voltage value 97 the amplifier 43 can be expected to output based on noise alone. (Noise in the sensor 10 may be caused by light scattered by gas molecules, by a change in intensity of the beam of light 13 or other causes.)

As an example and considering FIGS. 3, 4, and 5, the algorithm 85 will recycle in the state 89 until the latest sampled voltage value of a pulse like pulse 61 exceeds the noise level 97. This event indicates that a particle 31 is moving through the sensing volume 29 and is scattering light.

The way in which the peak value is ascertained is as follows. Continuing reference to FIG. 3, the algorithm 85 goes to the state 91 and cycles or recycles until it detects that the latest sampled value is less than the former sampled value. This event indicates that the peak of the pulse or waveform has occurred. Using values from Table 1, the 8th sampling yields a value of 97 and the 9th sampling a value of 81. Since the 9th sampling yielded the first, latest value which is less than the former value 97, the value 97 is used to ascertain, from Table 2 for example, the size of the particle 31 which caused the pulse. To put it another way, once the processor 49 detects a latest value which is less than the former value, the processor 49 "looks backward" one sample value to obtain the value of the peak.

Expressed in algebraic terms, the plurality of voltage values sampled includes 1 through "n" samples defining an arithmetic progression. The latest value is the sample "n" and the former value is the peak of the pulse and is the sample (n−1), i.e., that voltage value immediately prior to the latest value. Applying these algebraic terms to Table 1 and FIG. 3, the algorithm 85 would find particle size immediately after sampling the point 79 (sample "n") since it is the first sample after sampling the point 77 (sample n−1) in which the latest value is less than the former value.

For many types of pulses, sampling as depicted in FIG. 3 is effective for counting particles by size. However, a pulse may be much more irregular than the pulse 61 shown in FIG. 3. Unless sampled more frequently, the particle 31 counted may not be sized accurately.

Figure 6:
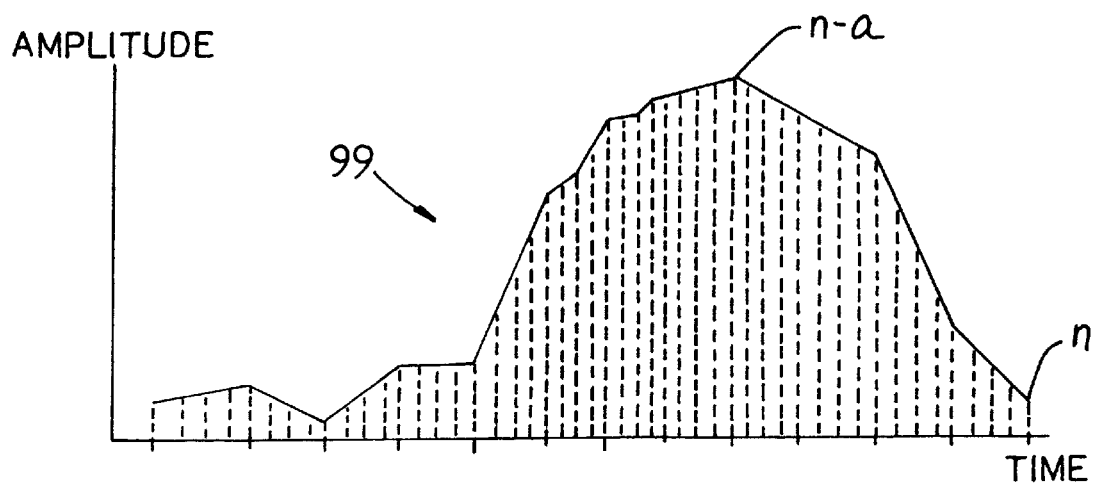
FIG. 6 is a graph generally like FIG. 3 showing how points along a voltage pulse are sampled much more rapidly than in FIG. 3.

A Referring also to FIG. 6, the plurality of voltage values sampled includes 1 through "n" samples also defining an arithmetic progression. The latest value is the sample "n" and the former value is the peak of the pulse and is the sample (n−a) where "a" is an integer between, e.g., 1 and 20 or between 1 and 10. In a specific method, the sample (n−a) has the largest voltage value of any of the samples 1 through n.

FIG. 6, a very-specific example, includes 49 samples of a pulse 99 so the sample "n" is the last or 49th sample. The peak of the pulse is at sample 33 so "a" in the formula is 16 (49−16=33). In a preferred aspect of the method, the establishing step includes identifying a noise-level voltage 97 and the finding step occurs when the latest value is less than the noise-level voltage. That is, the processor 49 will not "look back" for the peak value until the latest value has fallen to a level assuring that the particle 31 has passed through the sensing volume 29.

Particle Counting

The next task is to count, by its size, that particle, e.g., particle 31, which produced the pulse, e.g., pulse 61. The algorithm finds the correct count "bin" by comparing the former value (selected as the value of the peak) to the values in a table of thresholds such as that of Table 2. The largest threshold which the former value exceeds corresponds to that particle size bin and the count for that bin will be incremented. That is, a count of 1 will be added to that bin since one particle has just been detected to be of that particular size. Noting the example set out above, the processor 49 will count the particle 31 which produced the pulse resulting in the exemplary values of 97 and 81 as one having a size of between 0.6000μ and 0.7000μ and will add 1 to whatever the count is at that instant for particles of that size.

After counting a particle 31, the algorithm 85 enters the state 87 waiting for the end of the pulse 61 associated with the particle 31 just counted. In this state 87 the algorithm 85 will continue sampling the amplifier output until the latest value is below the baseline value 95. After the baseline value 95 has been reached, the algorithm 85 will again enter the state 89 of waiting for another pulse which exceeds the noise level 97. The algorithm 85 repeats until the processor receives a STOP command from the microcontroller 53.

It is to be noted here that counting the particle 31 upon the first occurrence of a latest sampled value which is less than the former sampled value is also useful in avoiding false counts caused by floaters or the like. Referring particularly to FIG. 5, the new particle sensor 10 is capable of distinguishing a bona fide particle 31 to be counted from a vagrant floater 33 or other anomaly. FIG. 5 shows an exemplary voltage pulse 101 that results from a floater 33 in the sensor 10 and also shows an exemplary voltage pulse 103 that results from a particle 31 passing through the sensor 10 in the fluid stream.

As is apparent, the voltage pulse 101 caused by a floater 33 does not return to the baseline value 95 quickly as does the pulse 103 caused by a particle. The pulse 101 may have additional peaks before finally returning to the baseline value 95. The algorithm 85 shown in FIG. 4 rejects these additional peaks by imposing the constraint that after detecting for the first time a latest value which is less than the former value, the output of the amplifier 43 return to the baseline value 95 before counting another particle 31.

Figure 7:
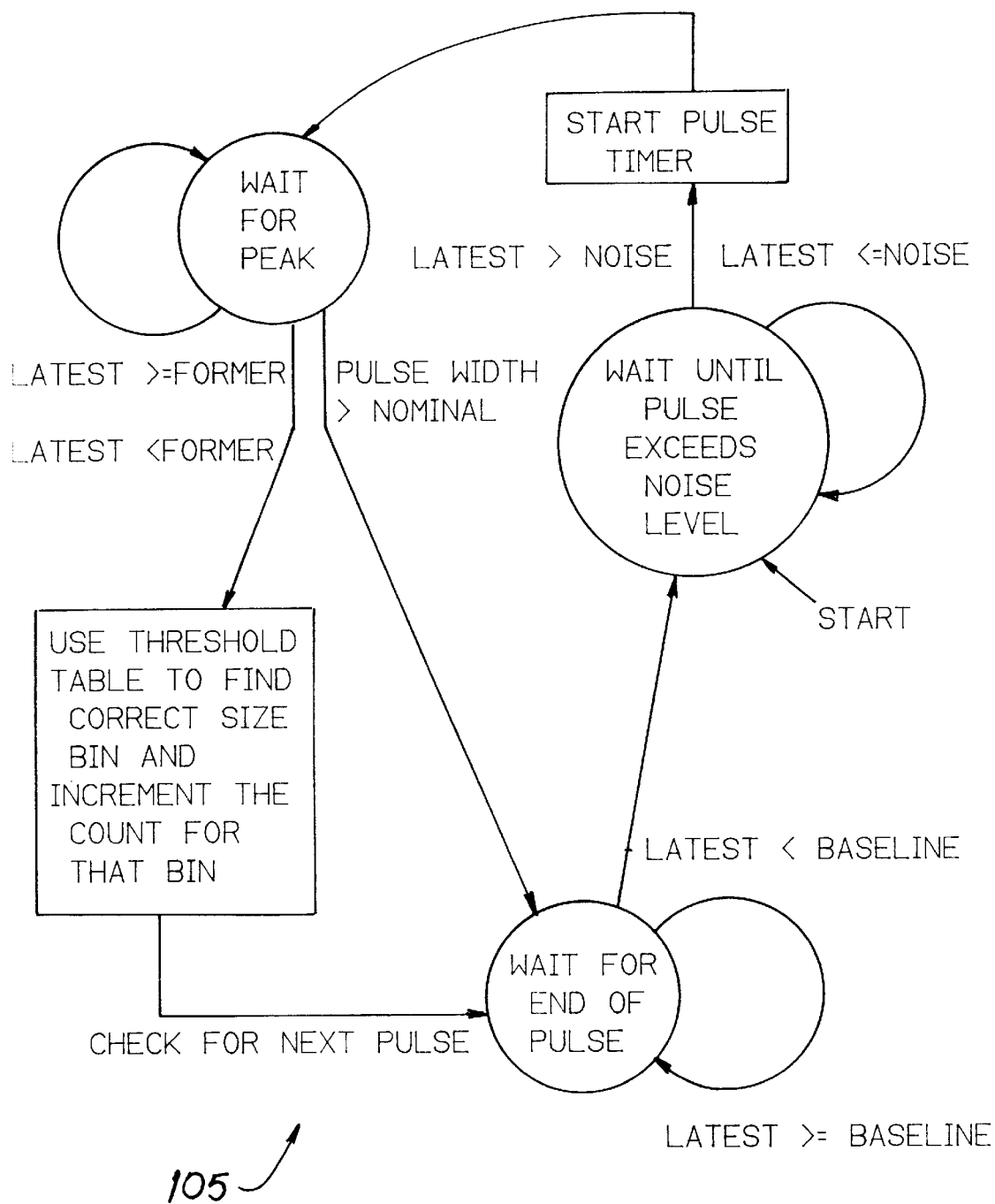
FIG. 7 shows, in diagram form, another of the algorithms with which the new sensor may be programmed.

Operation of Sensor with Algorithm of FIG. 7

Referring also to FIG. 7, another embodiment of the sensor 10 includes an algorithm 105 having an enhanced ability to reject floaters of other anomalies. This rejection is accomplished by requiring that the pulse from the amplifier have a certain maximum time duration before the circumstance of a latest value being less than the former value is interpreted as representing a particle 31 to be counted. As is apparent from the duration of the pulse 101, a floater 33 will typically produce a pulse, the duration of which is much longer than that of a pulse 103 produced by a particle 31 moving in the fluid stream and which is desired to be counted.

In the algorithm 105 diagrammed in FIG. 7, a pulse width timer is started as soon as a voltage value sampled on the pulse 101 or 103 exceeds the noise level. After an apparent pulse peak has been identified in one of the ways described above, the value of the pulse time will be compared to the nominal predetermined maximum value. If the value of the pulse time is found to exceed the predetermined maximum time, then the pulse will be disregarded, i.e., such pulse will not be interpreted as representing a particle to be counted.

Figure 8:
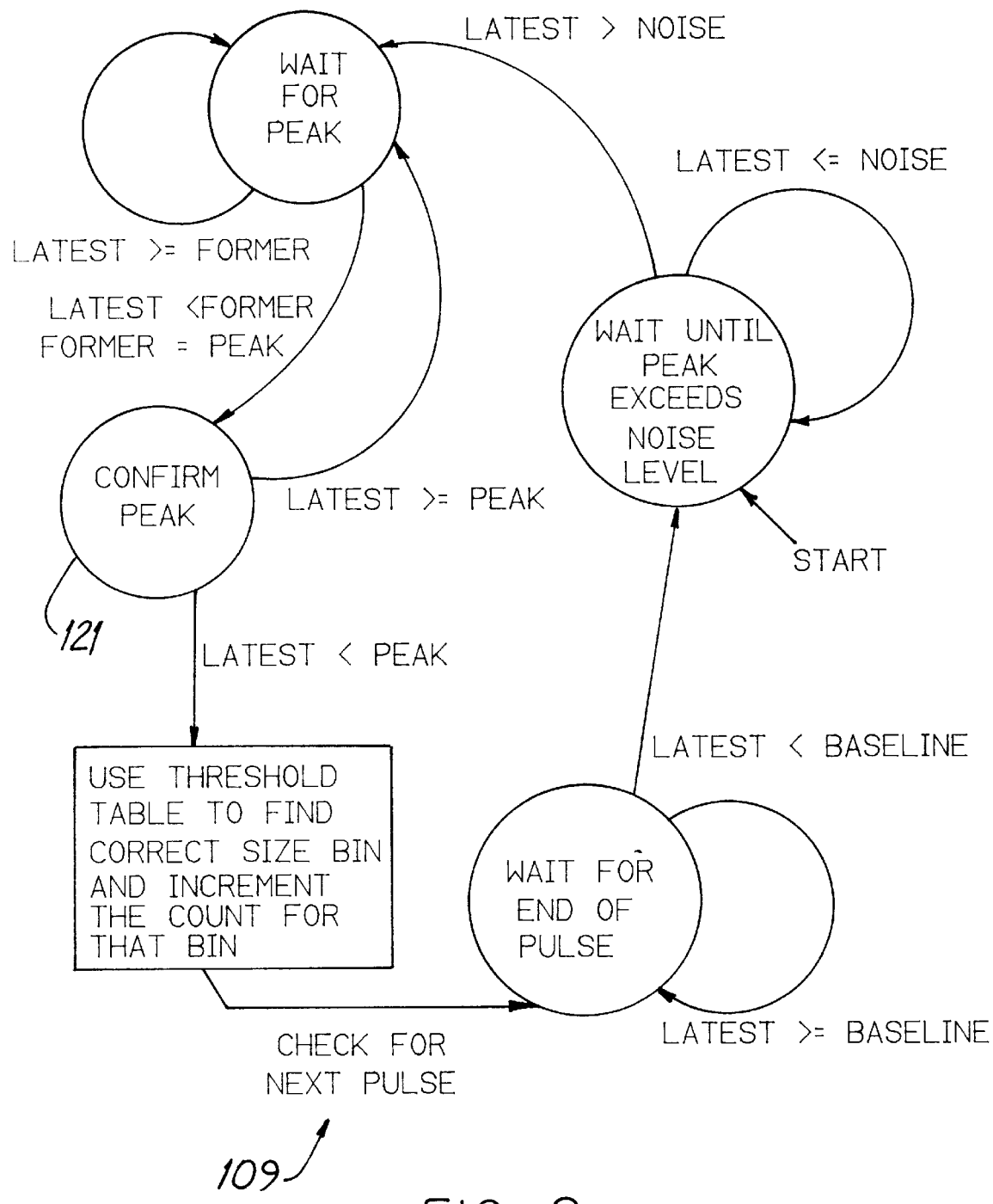
FIG. 8 shows, in diagram form, yet another of the algorithms with which the new sensor may be programmed.

Operation of Sensor with Algorithm of FIG. 8

Figure 9:
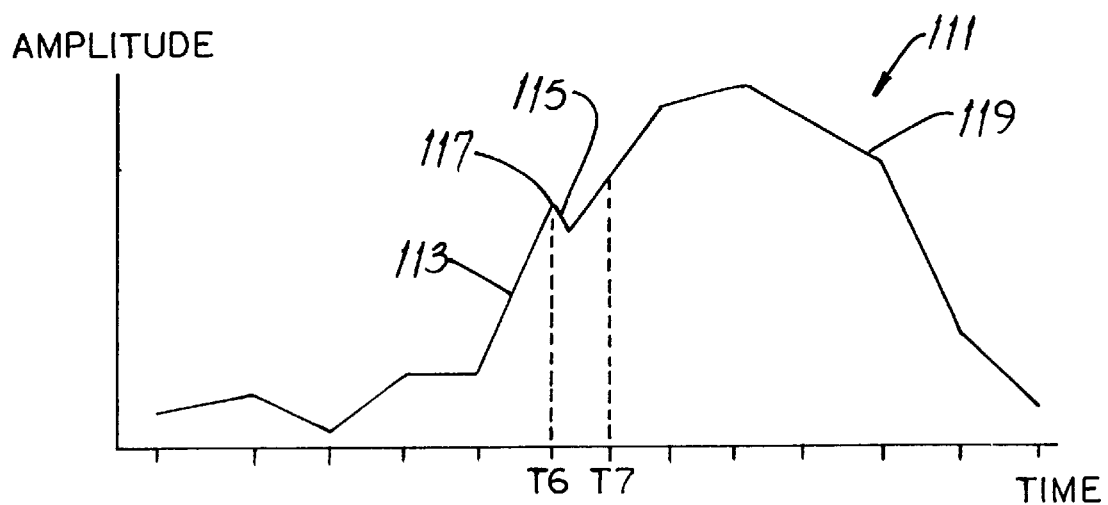
FIG. 9 is a graph showing how noise can influence the shape of a pulse caused by a particle.

Referring also to FIGS. 8 and 9, another embodiment of the sensor 10 includes an algorithm 109 exhibiting an enhanced ability to more accurately identify the peak value of a voltage pulse by rejecting noise. Noise on the rising edge 113 of a voltage pulse 111 could cause a momentary reversal, i.e., change of slope, as at 115. The resulting peak 117, even though a "false" peak not caused by a decline of the pulse 111 as at 119, might be misread as a peak by the algorithm 85 of FIG. 4.

This possible difficulty is overcome by the addition, in the algorithm 109 of FIG. 8, of a "Confirm Peak" state 121. After the peak 117 has been initially detected, the next sampled value must be less than the peak value 117 for the peak value to be interpreted as representing a particle to be counted. If this is not the case, the algorithm transitions back to the peak detection state.

For example, the sampling of the pulse value at the time T6 is seemingly of a bona fide peak 117. But when sampling the pulse value at time T7, it is apparent that such value is greater than the value of the peak 117. Therefore, the value sampled at time T6 is disregarded, i.e., the value is not interpreted as a peak caused by a particle 31 to be counted. When the noise is more severe, reversals may last for longer than a single sample period. In this case, the algorithm 109 is further modified by addition of more confirmation steps. Thus, noise spikes of a duration of several sample periods (or however many confirmation steps there are) can be rejected. When considering the above description, it should be noted that the algorithms 85, 105, 109 illustrated in FIGS. 4, 7, 8 can be combined so that an algorithm can have both the noise rejection and pulse width discrimination features.

The disclosed sensor 10 also permits the particle counter to be dynamically reconfigured by changing the value and number of the thresholds which define the particle size bins. In other words, the data of Table 2 can be changed.

To do so, the host computer 55 sends to the microcontroller 53 a calibrate command which includes the number of particle size bins and their thresholds. The microcontroller 53 will then communicate this information to the processor 49 so that it updates its threshold table values. These thresholds will then be used by the counting algorithm described above to sort the counted particles into their new size bins. This type of dynamic reconfiguration is different from that described in the Borden et al. '558 patent noted above which alters only the amplifier analog gain/bandwidth based on the external sampling conditions.

While the principles of the invention have been shown and described in connection with a few preferred embodiments, it is to be understood clearly that such embodiments are by way of example and are not limiting.

What is claimed:

1. A method for counting, by ranges of size, particles flowing through a particle sensor including the steps of:

projecting a stationary beam of light through a sensing cavity in the sensor;

establishing particle size ranges in a computerized table of particle sizes and corresponding voltages;

flowing a particle throughthe beam of light;

sampling, over an indeterminate period of time, a plurality of voltage values along a voltage pulse, the plurality of voltage values including a latest value and a former value preceding the latest value;

comparing the latest value with the former value;

finding, in the table, the size range for the particle, the finding step occurring upon determining that the latest value sampled is less than the former value sampled; and incrementing a counting bin corresponding to the size range for the particle.

2. The method of claim 1 wherein:
the establishing step includes identifying a noise-level voltage; and
the finding step occurs only when the latest value exceeds the noise-level voltage.

3. The method of claim 2 wherein:
the establishing step includes identifying a baseline voltage; and
repeating the finding and incrementing steps, such repeating occurring only after the latest value is below the baseline voltage, thereby substantially reducing false counts caused by vagrant particles.

4. The method of claim 3 wherein the voltage pulse has a duration and wherein:
the sampling step includes starting a timer when any of the plurality of voltage values exceeds the noise-level voltage;
and wherein the finding step occurs only if:
the duration of the pulse is not greater than some predetermined maximum time, thereby substantially reducing false counts caused by vagrant particles.

5. The method of claim 2 wherein the voltage pulse has a duration and wherein:
the sampling step includes starting a timer when any of the plurality of voltage values exceeds the noise-level voltage;
and wherein the finding step occurs only if:
the duration of the pulse is not greater than some predetermined maximum time, thereby substantially reducing false counts caused by vagrant particles.

6. The method of claim 1 wherein:
the establishing step includes identifying a baseline voltage; and
repeating the finding and incrementing steps, such repeating occurring only after the latest value is below the baseline voltage, thereby substantially reducing false counts caused by vagrant particles.

7. The method of claim 1 wherein the voltage pulse has a duration and wherein:
the establishing step includes identifying a noise-level voltage;
the sampling step includes starting a timer when any of the plurality of voltage values exceeds the noise-level voltage;
and wherein the finding step occurs only if:
the duration of the pulse is not greater than some predetermined maximum time, thereby substantially reducing false counts caused by vagrant particles.

8. The method of claim 1 wherein:
the pulse has a peak value;
the plurality of voltage values sampled includes l through "n" samples defining an arithmetic progression; and
the latest value is the sample "n" and the former value is the sample (n−1) and is the peak value.

9. The method of claim 1 wherein:
the pulse has a peak value;
the plurality of voltage values sampled includes l through "n" samples defining an arithmetic progression; and
the latest value is the sample "n" and the former value is the peak value and is the sample (n−a) where "a" is an integer.

10. The method of claim 9 wherein "a" is an integer between 1 and 20.

11. A particle sensor using scattered light for counting, by ranges of size, particles entrained in fluid drawn from an environment into the particle sensor, such sensor including:
an inlet through which a particle is drawn from the environment;
a sensing volume defined by the intersection of a stationary light beam and a fluid stream flowing from the inlet;
an exhaust port through which the fluid exits the sensor after passing through the sensing volume;
an optical light collection system redirecting light scattered by the particle in the sensing volume to a photo detector circuit which emits an electrical pulse representing the size of the particle;
an analog-to-digital converter coupled to the circuit and sampling the pulse at least twice;
a digital signal processor coupled to the converter; and
a microcontroller coupled to the processor;
and wherein the processor and the microcontroller are programmed to carry out a method for counting, by ranges of size, the particles flowing through the particle sensor, the method including the steps of:
establishing particle size ranges in a computerized table of particle sizes and corresponding voltages;
flowing a particle through the stationary beam of light;
sampling, over an indeterminate period of time, a plurality of voltage values along a voltage pulse;
comparing the latest value with the former value preceding the latest value;
finding, in the table, the size range for the particle, the finding step occurring upon determining that the latest value sampled is less than the former value sampled; and
incrementing a counting bin corresponding to the size range for the particle.

12. The sensor of claim 11 wherein the processor and the microcontroller are also programmed to execute the method wherein:
the establishing step includes identifying a noise-level voltage; and
the finding step occurs only when the latest value exceeds the noise-level voltage.

13. The sensor of claim 12 wherein the processor and the microcontroller are also programmed to execute the method wherein:
the establishing step includes identifying a baseline voltage; and
repeating the finding and incrementing steps only after the latest value is below the baseline voltage, thereby substantially reducing false counts caused by vagrant particles.

14. The sensor of claim 13 wherein the voltage pulse has a duration and the processor and the microcontroller are also programmed to execute the method wherein:
the sampling step includes starting a timer when any of the plurality of voltage values exceeds the noise-level voltage;
and wherein the finding step occurs only if:
the duration of the pulse is not greater than some predetermined maximum time, thereby substantially reducing false counts caused by vagrant particles.

15. The sensor of claim 12 wherein the voltage pulse has a duration and the processor and the microcontroller are also programmed to execute the method wherein:
the sampling step includes starting a timer when any of the plurality of voltage values exceeds the noise-level voltage;

and wherein the finding step occurs only if:
the duration of the pulse is not greater than some predetermined maximum time, thereby substantially reducing false counts caused by vagrant particles.

16. The sensor of claim 11 wherein the processor and the microcontroller are also programmed to execute the method wherein:
the establishing step includes identifying a baseline voltage; and
repeating the finding and incrementing steps, such repeating occurring only after the latest value is below the baseline voltage, thereby substantially reducing false counts caused by vagrant particles.

17. The sensor of claim 16 wherein the voltage pulse has a duration and the processor and the microcontroller are also programmed to execute the method wherein:
the sampling step includes starting a timer when any of the plurality of voltage values exceeds the noise-level voltage;
and wherein the finding step occurs only if:
the duration of the pulse is not greater than some predetermined maximum time, thereby substantially reducing false counts caused by vagrant particles.

18. The sensor of claim 11 wherein the voltage pulse has a duration and the processor and the microcontroller are also programmed to execute the method wherein:
the establishing step includes identifying a noise-level voltage;
the sampling step includes starting a timer when any of the plurality of voltage values exceeds the noise-level voltage;
and wherein the finding step occurs only if:
the duration of the pulse is not greater than some predetermined maximum time, thereby substantially reducing false counts caused by vagrant particles.

19. The sensor of claim 11 further including a host computer coupled to the microprocessor and wherein the processor and microcontroller are also programmed to execute the method wherein the incrementing step is followed by the step of:
initiating the host computer to change the particle size ranges in the table of threshold voltages.

20. The sensor of claim 19 wherein the processor and microcontroller are also programmed to execute the method wherein the initiating step includes initiating the host computer to change the threshold voltages.

* * * * *